United States Patent [19]

Price, Jr.

[11] Patent Number: 4,995,114
[45] Date of Patent: Feb. 26, 1991

[54] UNIVERSAL EYE PATCH

[76] Inventor: James A. Price, Jr., 26 Windwood Hill, Jackson, Tenn. 38305

[21] Appl. No.: 466,246

[22] Filed: Jan. 17, 1990

[51] Int. Cl.[5] .................. A61F 9/00; A61F 13/12
[52] U.S. Cl. ........................................ 2/15; 128/858
[58] Field of Search ............ 2/15; 128/858, 163, 128/155, 857

[56] References Cited

U.S. PATENT DOCUMENTS

| | | | |
|---|---|---|---|
| 2,165,668 | 7/1939 | Vaccaro | 2/15 |
| 2,572,638 | 10/1951 | Loos | 128/163 |
| 3,068,863 | 12/1962 | Bowman | 128/858 |
| 3,092,103 | 6/1963 | Mower | 128/858 |
| 3,952,735 | 4/1976 | Wirtschafter et al. | 128/163 |
| 4,134,401 | 1/1979 | Galican | 128/863 |
| 4,599,746 | 7/1986 | Stoner | 2/15 |
| 4,649,908 | 3/1987 | Ghaly | 128/858 |
| 4,682,371 | 7/1987 | Heltman | 2/15 |
| 4,793,003 | 12/1988 | Riedel et al. | 2/15 |
| 4,862,902 | 9/1989 | Goffman | 128/858 |
| 4,898,162 | 2/1990 | Worthrich | 2/15 X |
| 4,907,580 | 3/1990 | Leonardi | 128/163 |

FOREIGN PATENT DOCUMENTS 1048382 12/1953 France.

OTHER PUBLICATIONS

Instructions for application of "presspatch TM" by Precision Therapeutics, Inc., Las Vegas, Nev. 89109.

Primary Examiner—Peter Nerbun
Attorney, Agent, or Firm—Luedeka, Hodges & Neely

[57] ABSTRACT

An improved universal eye patch which may be successfully applied to either the right or the left eye. The eye patch comprises a central portion, preferably nonyielding, which serves to provide support to an underlying pad, and wing portions that extend angularly from the central portion and serve as means for securing the patch in position over the eye orbit. In the preferred patch, the wing portions are elastically stretchable in a direction away from the central portion and bear adhesive on their respective surfaces disposed in contact with the face so as to anchor the patch and maintain it tautly in position over the eye orbit.

14 Claims, 2 Drawing Sheets

UNIVERSAL EYE PATCH

This invention relates to eye patches employed by medical personnel in prophylactic and/or post-injury treatment of the eye. Specifically, this invention relates to an improved universal eye patch, i.e. an eye patch which may be applied to either the right or left eye with equal effectiveness, and to such an eye patch having an improved pad structure associated therewith.

Eye patches for medical purposes generally are employed for the purpose of maintaining the eyelid in its closed position inasmuch as such closed position is generally most desirable in enhancing the healing of an injured eye and in the prevention of further injury to the eye. Prior art eye patches include body members designed to be secured in covering relation to the eye as by means of adhesive, and body members provided with an elastic band designed to extend around the head and hold the patch in position over the eye. Known types of these prior art patches include body members that are generally oval or cup-shaped and fail to properly fit the eye socket, hence do not apply the correct pressure to the eyelids to maintain the eyelids closed.

To assist in developing the pressure against the eyelid to keep it in the desired closed position, most all eye patches include a compressible pad on the reverse side thereof (next to the eye) which is intended to contact the eyelid and be forced thereagainst by the eye patch body with a pressure sufficient to keep the eyelids from opening. The pads of the prior art have been oversized due to the relatively non-conforming nature of the eye patch body with which the pad is employed and the fact that such prior art patches are incapable of properly urging the pad into the desired pressure contact with the eyelids. The result most often has been that the pad and patch combination is bulky, difficult to apply and not satisfactorily effective.

In accordance with the present invention, there is provided an improved eye patch which may be successfully applied to either the right or left eye. Such eye patch comprises a central portion which serves to provide support to an underlying pad, and wing portions that extend angularly from the central portion and serve as means for securing the patch in position over the eye orbit. The central portion preferably is non-yielding and has associated therewith a pad element which preferably is of an oval geometry and possesses width and thickness dimensions that permit the central portion of the patch to urge the pad into the desired pressure relationship with the eyelids to maintain the eyelids closed. In the preferred patch, the wing portions are elastically stretchable in a direction away from the central portion so that when the wing portions are anchored to the patient's face the patch is maintained tautly in position over the eye orbit. Also preferably, the wing portions bear adhesive on their respective surfaces disposed in contact with the face to anchor the patch over the eye. Still further, in one embodiment, the pad itself is provided with an adhesive or other frictional material on that surface of the pad which engages the eyelids, thereby providing a means whereby the engagement of the pad with the eyelids is enhanced in a manner that assists in keeping the eyelids in their closed position when the patch is applied to the eye.

Further advantages and functions of the present invention will be recognized from the description contained herein, including the figures in which.

Figure 1:
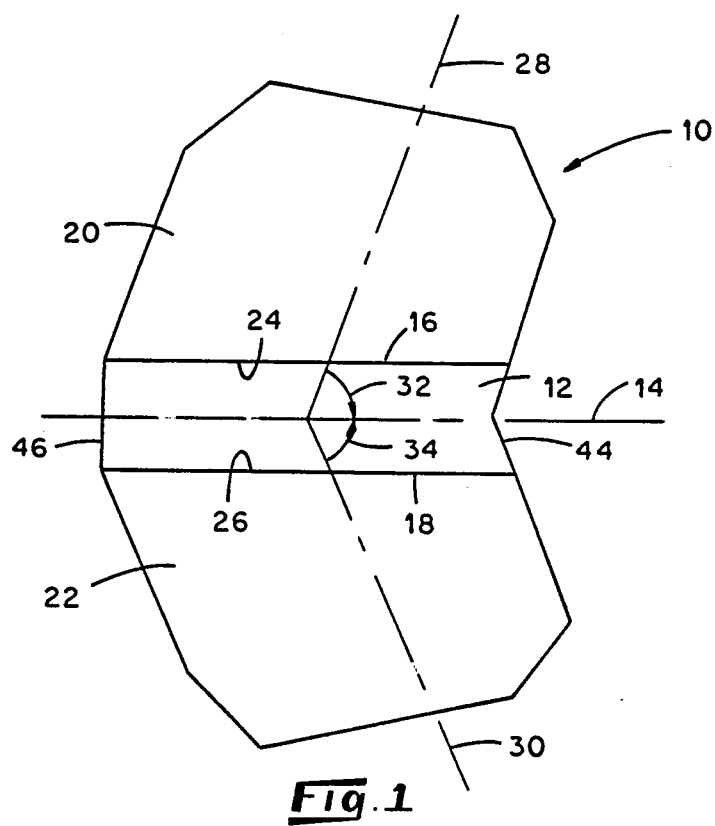
FIG. 1 is a plan view of the outer surface of an eye patch embodying various of the features of the present invention.

With reference to the several figures, in FIG. 1 there is depicted an eye patch 10 embodying various features of the invention. The depicted eye patch 10 comprises a central portion 12 which preferably is of a generally rectangular geometry having its length dimension 14 oriented generally horizontally when the eye patch is applied to an eye. As depicted, the central portion 12 includes opposite side edges 16 and 18 that are oriented generally parallel to the length dimension 14 of the central portion. The central portion 12 preferably is formed from a flat non-yielding material, preferably flexible. Woven cotton cloth serves quite adequately, but other materials having similar physical properties may be employed, for example, a plastic sheet material. In any event, the length dimension 14 of the central portion 12 is preferably chosen to cause the central portion to extend substantially fully across the eye orbit when the patch is applied thereto. Whereas in the preferred embodiment, the central portion is non-yielding, it is recognized that such central portion alternatively be of an elastic material, but in such instance there is some loss of control over the degree of tautness of the patch when applied to the eye.

Wing portions 20 and 22, each of a sheet-like material, and each having a side edge 24 and 26, respectively, are attached to and extend from the opposite side edges 16 and 18 of the central portion 12. Each wing portion 20 and 22 is of a generally rectangular geometry and includes a width dimension 28 and 30 which is parallel to an outer edge portion, respectively, which, when extended, defines an included angle 32 and 34, respectively, with the central portion 12 whereby the wing portions 20 and 22 extend from opposite sides of the central portion and over the frontal, maxillary and/or zygomatic bone structures of the eye when the eye patch is applied to an eye. When the eye patch is applied, the wing portions 20 and 22 slant outwardly away from the nasal region to more effectively urge the eye patch into full covering relationship to the eye orbit without leaving a substantial open space between the patch and the eye orbit in that region of the orbit adjacent the nose as is common in the prior art eye patches. Each wing portion preferably is formed of an elastically stretchable material, for example a strip of elastic adhesive tape. One such tape is sold by 3M Company under the brand name Transpore. This tape stretches both laterally and longitudinally, but it is only required that the material be stretchable in a direction parallel to the length dimension of the wing portion.

In a preferred embodiment, the central portion 12 has a length dimension of between about 2 inches and about 2½ inches, most preferably about 2¼ inches, and a width dimension of between about ½ inch and about ¾ inch, most preferably about ⅝ inch. The wing portions 20 and 22 may be, and preferably are, of like dimensions one with the other, but are mirror images of one another.

Each wing portion in a preferred embodiment has a width dimension of between about 1¾ inches and about 2 inches, most preferably about 2 inches, and a length dimension of between about 2 and about 2½ inches, most preferably about 2¼ inches. Each of the included angles 32 and 34 is between about 65 and about 75 degrees and most preferably about 70 degrees.

Figure 2:
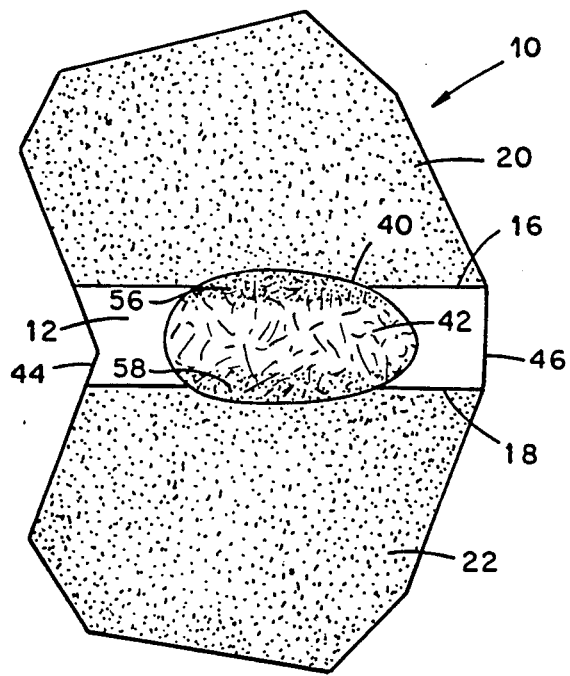
FIG. 2 is a plan view of the reverse or inner surface of the eye patch depicted in FIG. 1 and showing a pad associated with such surface.

With reference to FIG. 2, there is depicted the reverse side of the eye patch of FIG. 1. In FIG. 2, there is shown an eye pad 40 of generally oval or egg-shaped geometry, associated with the central portion 12 of the eye patch 10. As further depicted in FIG. 4, the eye pad 40 comprises a quantity of fibrous material 42, for example a ball of cotton or fibrous polyester, that is absorbent and gentle to the eye and eyelids when the pad is pressed against the eyelids upon application of the patch to the eye orbit. The length and width dimensions of the pad are chosen such that the pad does not extend materially out of the eye orbit when the patch is applied. To this end, a pad 40 having a length of between about 1¼ and about 1¾ inch, most preferably about 1½ inches, and a maximum width of between about 15/16 and about 1¼ inches, most preferably about 1-1/16 inches, when uncompressed is employed. Thus, the width (i.e. lateral) dimension of the pad is not subtantially greater than the width of the central portion 12. The thickness of the pad 40 is chosen to provide sufficient volume of the fibrous material such that when the patch 12 is applied to the eye 50 with the pad 40 captured within the eye orbit 51 between the central portion 12 and the eyelids, there is sufficient pressure applied to the eyelids 53 and 55 (see FIG. 4) by the pad to maintain the eyelids closed, but not so great a pressure as to be detrimental to the desired conditions for healing nor to be painful (See FIG. 4). An uncompressed thickness dimension of the pad 40 of between about ⅞ and about 1¼ inch, compressible to about ¾ inch, has been found to be most suitable, with the preferred thickness being about 1 inch. By reason of the preferred indicated size dimensions of the pad, plus its geometry, the pad is substantially fully received within the eye orbit, thereby positioning the pad for its most effective performance. Recognizing that a major function of the pad is to maintain the eyelids closed, it is important that the pad be formed of a material that resists the shear forces applied thereagainst when a patient attempts to open the eyelids. Accordingly, in the preferred pad, the fibrous material is entangled and/or intertwined so that the pad retains its integrity under shear. As desired, the fibrous pad may be provided with a gauze covering for strength and to reduce linting of the pad. Preferably, the pad 40 is adhesively secured to the central portion 12 thereby facilitating proper positioning of the pad in the course of applying the patch over the eye. Further, as depicted by the stippling in FIG. 2, that surface of the pad 40 which is intended to face the eyelids is provided with an adhesive or other frictional material, e.g. sponge rubber coating. In the depicted embodiment, such adhesive comprises two areas 56 and 58 of adhesive, one area of adhesive 56 being spaced apart from the other area 58 to provide an adhesive-free zone therebetween to receive the eyelashes (not shown). As desired, the entire reverse surface of the pad may be covered by the frictional material.

Preferably the eye patch of the present invention is provided to the end user as a sterile product. Therefore, preferably all materials of construction of the patch and pad are sterilizable.

Figure 3:
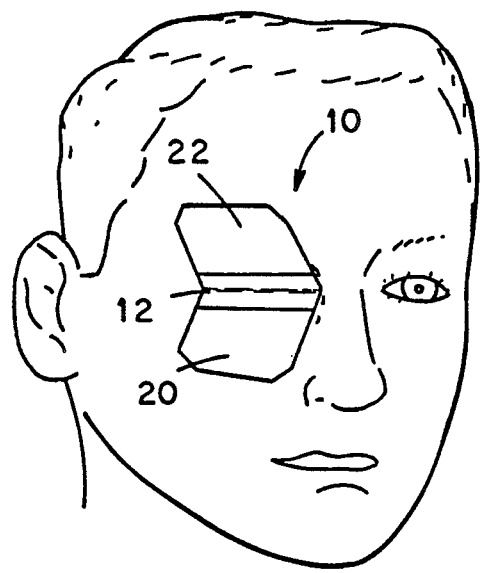
FIG. 3 is a schematic representation of an eye patch in accordance with the present invention as applied to an eye; and, FIG. 4 is a fragmentary sectional representation of an eye patch in accordance with the present invention as applied to an eye.
Figure 4:
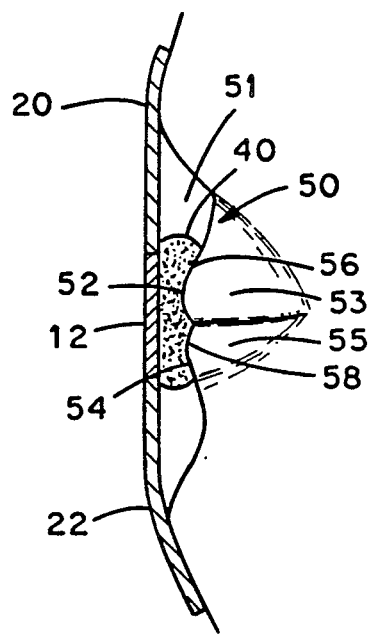

In FIGS. 3 and 4, there is depicted an eye patch 10 applied to an eye 50. In these figures it may be seen that the present patch 12 is designed to substantially fully cover the eye orbit 51 with the length dimension of the central portion 12 thereof extending generally horizontally and substantially fully between the lateral limits of the eye orbit. One wing portion 20 extends downwardly from the central portion 12 and overlies the maxillary and/or zygomatic bone structures which define the lower portion of the eye orbit. The other wing portion 20 extends upwardly from the central portion and overlies the frontal bone structure that defines the upper portion of the eye orbit. Notably, each of the wing portions 20 and 22 further extend outwardly from the eye orbit away the nasal region thereby ensuring that the central portion of the patch fully covers that part of the eye orbit adjacent the nose.

As best seen in FIG. 4, when the patch is applied to cover the eye orbit 51, the pad 40 is captured between the central portion 12 of the patch and the eyelids 52 and 54. The depicted pad 40 is provided with adhesive (indicated by the stippling in FIG. 2) on that surface of each wing portion 20 and 22. This adhesive bearing surface is applied to the skin of the patient in the course of applying the patch over an eye. By reason of the stretchable, preferably elastic, nature of the wing portions 20 and 22, the patch, anchored by its adhesive-bearing wing portion, is maintained taut across the eye orbit. By this means, the pressure applied to the pad 40 by the central portion 12 is maintained substantially constant. This allows selection of the optimum thickness of the pad as will develop the desired pressure against the eyelids to keep the eyelids closed, but without undue and deleterious pressure against the eye itself. As desired, the patch may be provided to the end user with pads of different thicknesses to permit selection of the optimum pad-patch combination. Further, whereas the use of adhesive wing portions is preferred, it is recognized that other means of anchoring the wing portions to the patient's face may be employed, for example adhesive tape strips. As noted, a frictional material 56 and 58 may be applied to the reverse surface of the pad 40 to enhance its frictional engagement with the closed eyelids 53 and 55.

The present pad is designed to be universal, that is, it may be applied equally effectively to either the left or right eye. To this end, as noted, the wing portions 20 and 22 are essentially mirror images so that the pad may be applied with the wing portion 22 in an uppermost position when applied to the right eye as depicted in FIG. 3 or the patch may be rotated 180 degrees to position the wing portion 20 in the uppermost position for applying the patch to the left eye.

Whereas specific embodiments have been depicted and described herein, such is not intended to be limiting of the invention except at defined in the claims appended hereto.

I claim:

1. An eye patch comprising a relatively non-yielding central portion having a length dimension, and first and second wing portions, each having a length dimension, connected to and extending from said central portion on opposite sides of said length dimension along said central portion, said first and second wing portions each having an outer edge portion which defines an included angle of between about 65 and 75 degrees with a respective elongated edge of said central portion whereby when said eye patch is disposed in covering relationship to the eye, said central portion extends generally horizontally across the opening of the eye orbit and said wing portions extend angularly outwardly away from the nasal region to anchor the patch across the opening of the eye orbit.

2. The eye patch of claim 1 and including means anchoring said wing portions to locations generally diametrically across the eye orbit.

3. The eye patch of claim 1 wherein said central portion is of a material which is relatively non-yielding.

4. The eye patch of claim 1 wherein said wing portions are each of a material that is elastically stretchable in a direction substantially parallel to said edge portion of each of said wing portions.

5. The eye patch of claim 4 wherein each of said wing portions comprises an elastic adhesive tape material.

6. The eye patch of claim 1 and including an eye pad associated with said central portion and disposed between said central portion and the eye when said patch is disposed in covering relationship with the eye.

7. The eye patch of claim 6 wherein said eye pad comprises a quantity of absorbent resilient material having lateral dimensions not substantially greater than the corresponding lateral dimensions of said central portion and a thickness sufficient to develop adequate pressure against the eyelids to maintain the eyelids closed when the eye patch is disposed in covering relationship to the eye with the eye pad captured between the eye patch and the eyelids.

8. The eye patch of claim 7 wherein said eye pad when uncompressed has a length dimension of between about $1\frac{1}{4}$ and about $1\frac{3}{4}$ inch, a maximum width dimension of between about 15/16 and about $1\frac{1}{4}$ inch, and a thickness dimension of between about $\frac{7}{8}$ and about $1\frac{1}{4}$.

9. The eye patch of claim 8 wherein said eye pad comprises a material selected from the group consisting of cotton and fibrous polyester.

10. The eye patch of claim 7 wherein said pad includes a frictional material on that surface thereof which contacts the closed eyelids.

11. The eye patch of claim 1 wherein said central portion has a length dimension of between about 2 and about $2\frac{1}{2}$ inches, and a width dimension of between about $\frac{1}{2}$ and about $\frac{3}{4}$ inch.

12. A universal eye patch suitable for substantially fully covering a human eye orbit and maintaining the underlying eyelids in the closed position comprising a body member including an elongated central portion of relatively non-yielding sterilizable material and of a length sufficient to extend substantially across the eye orbit in a generally horizontal direction, said central portion defining first and second sides disposed on opposite sides of a horizontal length dimension of said elongated central portion, and first and second wing portions secured to and extending from respective ones of said sides of said central portion respective distances sufficient to extend across the eye orbit in a generally vertical direction and serve as means for anchoring said eye patch on opposite sides of the eye socket, said first and second wing portions being substantially mirror images of one another and each having an outer edge portion which defines an included angle of between about 65 and about 75 degrees with a respective elongated edge of said central portion, and eye pad means associated with said central portion on that surface of said central portion facing the eye, said eye pad means comprising a quantity of absorbent material of a resilient nature and sufficient in volume and compacted density when held in position by said eye patch against the eyelids to develop sufficient pressure against the eyelids as to maintain the eyelids in the closed position, said eye pad means in its uncompressed state being of substantially oval geometry and having lateral dimensions not substantially greater than lateral dimensions of said central portion.

13. An eye patch in accordance with claim 12 wherein said first and second side portions are formed of a material which is elastically stretchable in a direction parallel to the outer edge portion of a respective side portion.

14. An eye patch in accordance with claim 12 wherein said first and second side portions each include an adhesive material on that surface thereof facing the eye, said adhesive material being suitable to secure said side portions to opposite sides of the eye orbit.

* * * * *